(12) United States Patent
Gao

(10) Patent No.: US 11,661,434 B2
(45) Date of Patent: May 30, 2023

(54) PHOSPHATE OF PLATINUM COMPOUND AND PREPARATION METHOD THEREFOR

(71) Applicant: Beijing Showby Pharmaceutical Co., LTD., Beijing (CN)

(72) Inventor: Zejun Gao, Beijing (CN)

(73) Assignee: BEIJING SHOWBY PHARMACEUTICAL CO., LTD., Beijing (CN)

(*) Notice: Subject to any disclaimer, the term of this patent is extended or adjusted under 35 U.S.C. 154(b) by 0 days.

(21) Appl. No.: 17/271,110

(22) PCT Filed: Aug. 28, 2019

(86) PCT No.: PCT/CN2019/103147
§ 371 (c)(1),
(2) Date: Feb. 24, 2021

(87) PCT Pub. No.: WO2020/043144
PCT Pub. Date: Mar. 5, 2020

(65) Prior Publication Data
US 2021/0253619 A1 Aug. 19, 2021

(30) Foreign Application Priority Data
Sep. 1, 2018 (CN) .......................... 201811017816.X

(51) Int. Cl.
C07F 15/00 (2006.01)
A61K 31/282 (2006.01)

(52) U.S. Cl.
CPC ........ *C07F 15/0093* (2013.01); *A61K 31/282* (2013.01); *C07B 2200/13* (2013.01)

(58) Field of Classification Search
None
See application file for complete search history.

(56) References Cited

U.S. PATENT DOCUMENTS

| 4,322,362 A | 3/1982 | Kaplan et al. |
| 9,138,421 B2* | 9/2015 | Chen ....................... A61P 35/00 |
| 2005/0197389 A1 | 9/2005 | Pepels et al. |
| 2006/0205677 A1 | 9/2006 | Gao et al. |

(Continued)

FOREIGN PATENT DOCUMENTS

| CN | 102863474 A | 1/2013 |
| CN | 104829653 A | 8/2015 |

(Continued)

OTHER PUBLICATIONS

Van der Sluis, P. Appl. Cryst. (1989). 22, 340-344.*
International Search Report for PCT/CN2019/103147 dated Dec. 6, 2019.
Indian Search Report for 202147008810 dated Apr. 20, 2021.
EP Search report for PCT/CN2019103147 dated Jun. 1, 2021.

(Continued)

*Primary Examiner* — Clinton A Brooks

(74) *Attorney, Agent, or Firm* — Thomase | Horstemeyer, LLP

(57) ABSTRACT

Provided is 2-(4-diethylamino)butylmalonic acid-(1R,2R)-(−)-1,2-cyclohexanediamine platinum(II) phosphate having high solubility, low hygroscopicity, and high stability and being suitable for preparing into various antitumor drug preparations. Also provided is a preparation method for amorphous 2-(4-diethylamino)butylmalonic acid-(1R,2R-)-1,2-cyclohexanediamine platinum(II) phosphate. The method is simple to operate and is suitable for industrial implementation.

11 Claims, 10 Drawing Sheets

(56) References Cited

U.S. PATENT DOCUMENTS

| | | |
|---|---|---|
| 2011/0269706 A1 | 11/2011 | Chen et al. |
| 2013/0236568 A1 | 9/2013 | Bose |
| 2014/0142079 A1 | 5/2014 | Chen et al. |
| 2015/0352220 A1 | 12/2015 | Reithofer et al. |
| 2015/0368281 A1 | 12/2015 | Chen et al. |
| 2018/0312534 A1 | 11/2018 | Sarkar et al. |

FOREIGN PATENT DOCUMENTS

| | | |
|---|---|---|
| CN | 105218587 A | 1/2016 |
| EP | 2924044 A1 | 9/2015 |
| JP | 2012-515776 A | 7/2012 |
| JP | 2014-523905 A | 9/2014 |
| RU | 2345085 C2 | 1/2009 |
| RU | 2648990 C1 | 3/2018 |
| WO | 2006/091790 A1 | 8/2006 |
| WO | 2013007172 A1 | 1/2013 |
| WO | 2013/041014 A1 | 3/2013 |
| WO | 2013/083058 A1 | 6/2013 |
| WO | 2014075391 A1 | 5/2014 |
| WO | 2014/114183 A1 | 7/2014 |
| WO | 2016210418 A1 | 12/2016 |

OTHER PUBLICATIONS

EP search report for EP 19854967 dated May 12, 2021.
Australian First Examination Report, Australian Application No. 2019326814, dated Sep. 2, 2021 (3 pages).
China First Office Action, CN Patent Application No. 201980051809.8, dated Aug. 4, 2021 (12 pages).
Second Office Action, issued by China Patent Office, China Patent Application No. 201980051809.8, dated Apr. 18, 2022 (10 pages).
Examination Report, issued by European Patent Office, EP Patent Application No. 19854967.7, dated May 16, 2022 (4 pages).
Office Action, issued from Japan Patent Office, JP Patent App. 2021-511557, dated Apr. 4, 2022 (7 pages).
Office Action, issued from Canadian Patent Office, CA Patent App. 3,110,611, dated Jun. 22, 2022 (6 pages).
Caron, Giulia, et al., "The Relevance of Polar Surface Area (PSA) in Rationalizing Biological Properties of Several cis-Diamminemalonatoplatinum(ii) Derivatives," Chem. Med. Chem., vol. 4 (2009), pp. 1677-1685.
Wenyi Zhao, "Handbook for Chemical Process Research and Development, Chapter 16—Pharmaceutical Salts," CRC Press (2016), pp. 769-786.
Berge, Stephen M., et al., "Pharmaceutical Salts," Journal of Pharmaceutical Sciences, vol. 66, No. 1 (1977) (19 pages).

\* cited by examiner

PHOSPHATE OF PLATINUM COMPOUND AND PREPARATION METHOD THEREFOR

CROSS-REFERENCE TO RELATED APPLICATIONS

The present application is a U.S. National Phase Entry of International PCT Application No. PCT/CN2019/103147 having an international filing date of Aug. 28, 2019, which claims priority to Chinese Patent Application No. 201811017816.X filed on Sep. 1, 2018. The present application claims priority and the benefit of the above-identified applications and the above-identified applications are incorporated by reference herein in their entirety

TECHNICAL FIELD

The present invention belongs to the field of medical technology, and particularly relates to 4-(diethylamino)butylmalonato-(1R,2R)-(−)-1,2-cyclohexanediamine platinum(II) phosphate, preparation method therefor and pharmaceutical compositions thereof.

BACKGROUND

Cancer (malignant tumor) is currently one of the most major diseases threatening human lives. Platinum-based antitumor drugs are the most important type of antitumor drugs. Cisplatin, carboplatin oxaliplatin, etc. have been successfully developed in succession. Statistical data shows that, 70%-80% of all current chemotherapy regimens consist of platinum-based drugs.

Lots of studies have been conducted in order to reduce the toxic and side effects of platinum-based chemotherapy drugs, improve curative effect, reduce tumor recurrence and avoid drug resistance, and also to improve water solubility of platinum compounds. For example, the solubility of cisplatin is 2.65 mg/ml, the solubility of oxaliplatin is 7.9 mg/ml, and the solubility of carboplatin is 17.8 mg/ml. Moreover, oxaliplatin, and carboplatin, etc. have reduced toxic and side effects, as compared with cisplatin. The deficiency is that the solubility of the above so-called water-soluble platinum compounds remains slightly soluble or sparingly soluble, and the antitumor activity thereof is far lower than that of cisplatin. Murray A. Plan et al. have prepared sodium alkoxide of platinum compounds, which effectively improved the solubility in vitro (U.S. Pat. No. 4,322,362A), but the compounds thereof can only be dissolved at a pH of 10 or above, and the problem of toxicity has still not been effectively solved. Giulia C et al. have also prepared a series of platinum compounds, but the solubility of these compounds has still not been significantly improved (Chem Med Chem, 2009, 4(10), 1677-1685). WO2006091790A1 also discloses a series of platinum compounds with specific structures, but also fails to solve the problems of solubility and toxicity.

WO2013007172A1, WO2013041014A1. WO2013083058A1. WO2014075391A1, WO2014114183A1, etc. disclose a series of water-soluble platinum compounds, which have a solubility of 50 mg/ml or more in water, and the solubility of some preferred compounds may reach 100 mg/ml or even 300 mg/ml or more.

WO2014075391A1 discloses in Example 3 the compound 4-(diethylamino)butylmalonato-(1R,2R)-(−)-1,2-cyclohexanediamine platinum(II), the tosylate, sulfate, mesylate, tartrate, succinate, acetate, citrate, etc, thereof, and the preparation method thereof. However, this compound is almost insoluble in solvents such as water, and slightly soluble in methanol, and the pH value is greater than 10. Thus, it is not suitable to be prepared into a pharmaceutical preparation for clinical use. After it is converted into salts with the above acids, the solubility is greatly improved, and the pH value is 3-5. However, it is highly hygroscopic in air and easy to deliquesce. Under the existing GMP production conditions, it is difficult to control the water content to produce bulk drug substances with reliable quality. Unexpectedly, the solubility of the phosphate salt in water is greater than 500 mg/ml, but the moisture absorption rate in air is lower than that of other salts, so the quality is controllable in the preparation process. For example, under the conditions of low relative humidity (RH44%) and high relative humidity (RH69%) in air for 1 hour, the moisture absorption of other salts mostly exceed 3% or even 5%, which exceeds the limit of water content of quality standard. It is an important condition for producing qualified raw materials that phosphate has stable properties after moisture absorption. For other salts, the properties will be easily changed after moisture absorption. In addition, in the preparation of the intermediate 4-(diethylamino)butyl malonate disalt, in the original reference, the product was not separated and the reaction solution was directly used for the next reaction, which is prone to cause inaccurate feeding amount and produce impurities. In the present invention, pure 4-(diethylamino)butyl malonate salt can be obtained by changing the solvent, which provides a good foundation for the quality control in the next reaction. Moreover, silver sulfate is used in the preparation of (1R,2R)-(−)-1,2-cyclohexanediamine platinum(II) dihydrate. Since the solubility of silver sulfate in water or other solvents is relatively low, a relatively large reaction volume is required for the chemical reaction, which is difficult for amplifying production, thereby limiting the production scale of the product. By using the improved method, the reaction volume is reduced to 40% of the original volume, and the purity of the yielded 2-(4-diethylamino)butylmalonato-(1R,2R)-(−)-1,2-cyclohexanediamine platinum(II) obtained reaches 99.5% or above.

In this invention, the crystalline forms of 4-(diethylamino)butylmalonato-(1R,2R)-(−)-1,2-cyclohexanediamine platinum(II) and various salts thereof are also determined, and the results show that X-ray powder diffraction patterns of the free base and various salts differ significantly, and the powder diffraction patterns of various salts also differ significantly. When the phosphate salt of the compound is crystallized using different solvents, the crystalline forms obtained are different (having different positions of diffraction peaks). Finally, lyophilization method is used to prepare the compound, and the crystalline form thereof exhibits stability when prepared on a large-scale. The stable crystalline form of phosphate was used to prepare a pharmaceutical preparation, and the X-ray powder diffraction pattern thereof was consistent with that of the raw material.

SUMMARY

One of the objects of the present invention is to provide a compound of Formula (1), namely 4-(diethylamino)butylmalonato-(1R,2R)-(−)-1,2-cyclohexanediamine platinum (II) phosphate.

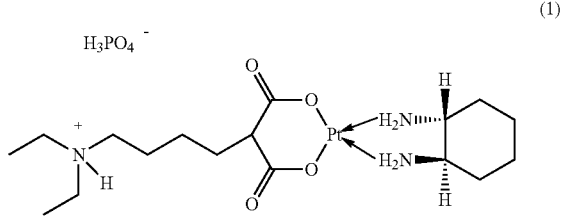

(1)

The compound of Formula (1) not only has solubility in water of greater than 500 mg/ml, but also has relatively low hygroscopicity in air, which is easy to be stored and facilitates the preparation into a pharmaceutical preparation for clinical use.

When the compound of Formula (1) is crystallized under different solvent conditions, different crystalline forms are obtained. The crystalline form with characteristic peaks of X-ray powder diffraction pattern shown in FIG. 6 is preferred, which is stable and has good reproducibility.

Another object of the present invention is to provide a method for preparing the compound of Formula (1), including the following steps:

(I) preparing a 4-diethylamino butyl malonate disalt solution according to the method disclosed in International Publication No. WO2014075391A1, and adding a solvent to crystallize and obtain 4-diethylamino butyl malonate disalt, wherein the solvent is selected from methanol, ethanol, isopropanol, acetonitrile, acetone, dimethyl sulfoxide (DMSO), etc. or mixtures thereof, preferably ethanol:

(2) preparing (1R,2R)-(−)-1,2-cyclohexanediamine platinum(II) dihydrate salt by: preparing (1R,2R)-(−)-1,2-cyclohexanediamine diiodoplatinum(II) according to the method disclosed in International Publication No. WO2014075391A1, and reacting (1R,2R)-(−)-1,2-cyclohexanediamine diiodoplatinum(II) with silver nitrate in a solvent to obtain (1R,2R)-(−)-1,2-cyclohexanediamine platinum(II) dihydrate salt, wherein the molar ratio of (R,2R)-(−)-1,2-cyclohexanediamine diiodoplatinum(II) to silver nitrate is 1-3.1, preferably 1:1; the solvent is selected from water, methanol, ethanol, isopropanol, etc., preferably water; and the reaction temperature ranges from 0° C., to 60° C., preferably from 40° C., to 50° C., and the reaction time is 2-10 hours, preferably 5-6 hours;

(3) preparing the compound of Formula (1) according to the method disclosed in International Publication No. WO2014075391 A1 using (4-diethylamino)butyl malonate disalt and (1R,2R)-(−)-1,2-cyclohexanediamine platinum (II) dihydrate salt, and (4) dissolving the compound of Formula (1) in water, followed by lyophilization to obtain a final crystalline product.

A further object of the present invention is to provide a pharmaceutical composition comprising the compound of Formula (1).

The preparation of the pharmaceutical composition of the present invention includes, but is not limited to, lyophilized powder, filled packages of bulk drug substance and injection, and when in use, the lyophilized powder and filled packages of bulk drug substance are added with 5% glucose or mannitol infusion for intravenous drip.

The present invention further provides a pharmaceutical preparation for injection containing a crystalline solid of the compound of Formula (1). The pharmaceutical preparation for injection contains 0.002%-100%, preferably 5%-100%, most preferably 25%-100% (by weight) of the compound of Formula (1), and the remainder consists of appropriate pharmaceutical carriers and/or excipients. A pharmaceutical preparation for injection can be prepared by a method well known in the art using suitable carriers and/or excipients and the compound of Formula (1). Examples of suitable excipients include, but are not limited to, lactose, glucose, sucrose, sorbitol, mannitol, phosphate buffer, and the like. The results of prescription studies show that various carriers and/or excipients, such as glucose, phosphate buffer, etc., have no significant effect on the appearance and properties and related substances of the product. Therefore, it is preferable not to add any carrier and/or excipient to the preparation process.

The amount of the compound of Formula (1) in a unit dose preparation may vary between 10 mg and 1000 mg, preferably between 50 mg and 1000 mg, and most preferably between 100 mg and 500 mg.

The pharmaceutical preparation for injection containing the compound of Formula (1) may be repeatedly administered, for example, at least 2, 3, 4, 5, 6, 7, 8 or more times, or the pharmaceutical preparation for injection may be administered through continuous infusion. The preparation may be in the form of sterile injection and sterile packaged powder. Preferably, the injection is formulated at a pH of 4.0-7.5.

The pharmaceutical preparation of the present invention in the form of sterile injection may be prepared according to a known technology in the field using suitable diluents or solvents. Acceptable vehicles and solvents that can be used include deionized solution such as water, glucose solution, mannitol solution, etc. The pharmaceutical preparation of the present invention in the lyophilized form may also be provided.

The above pharmaceutical preparation may further include other active ingredients for treating or assisting in the treatment of proliferative diseases, or may be used in combination with other drugs for treating or assisting in the treatment of proliferative diseases, for example, used in combination with anti-proliferative agents, immunomodulators, anticancer drugs, cytotoxic agents, and antitumor adjuvant drugs other than the present invention.

DETAILED DESCRIPTION

Figure 1:
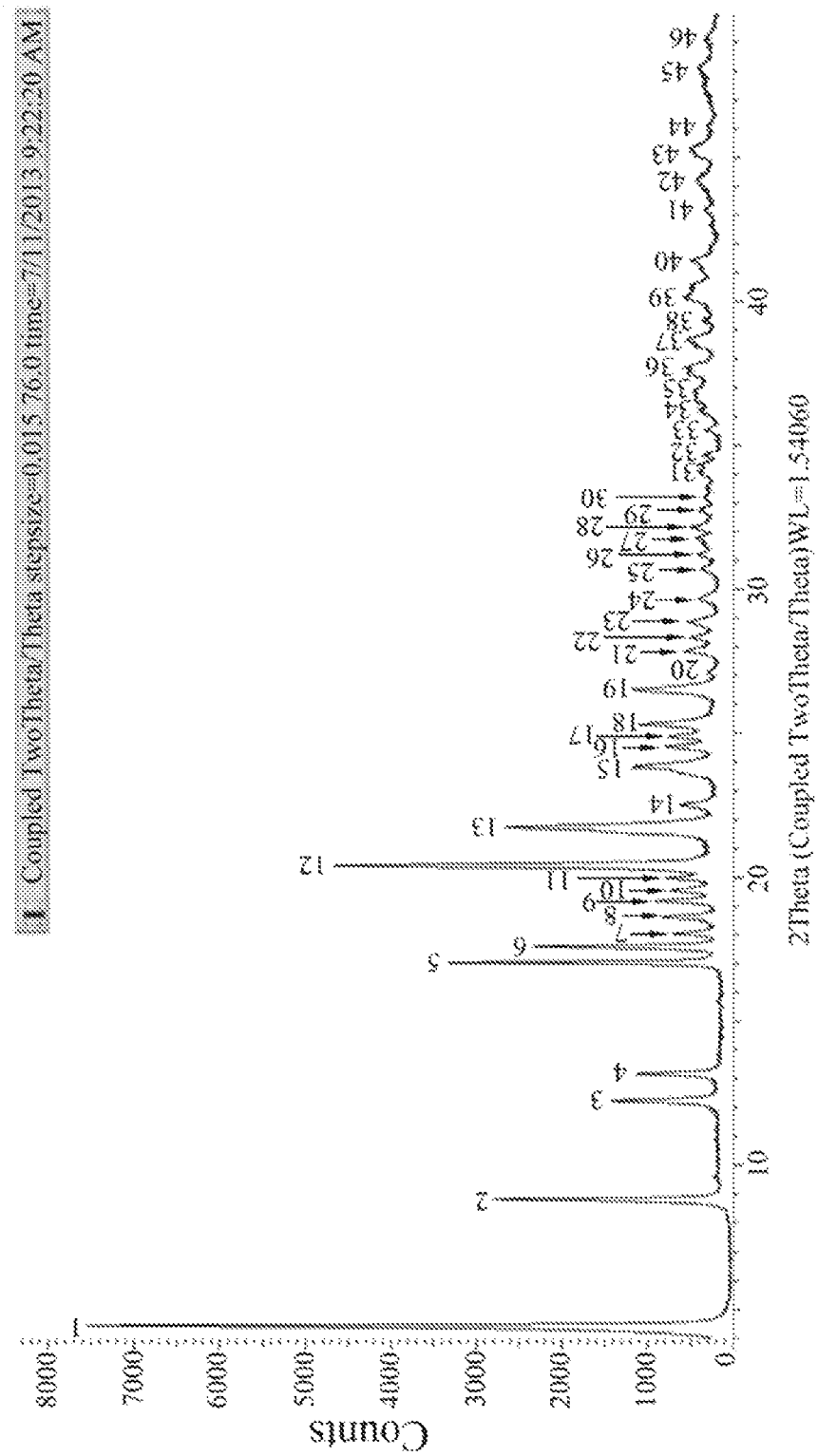
FIG. 1: X-ray powder diffraction pattern of (4-diethylamino)butylmalonato-(1R,2R)-(−)-1,2-cyclohexanediamine platinum(II).

The present invention will be described in further detail below with reference to examples and accompanying drawings. However, the embodiments of the invention do not limit the scope of the present invention in any way.

The determination of crystalline form of various compounds in the examples is carried out using a powder X-ray diffraction analyzer (Bruker D8 advance) equipped with a LynxEye detector. The 2θ scan angle of the sample is from 3° to 40°, the scan step is 0.02°, and the voltage and current of the light tube are 40 kV and 40 mA, respectively. Samples are tested using a zero background sample holder. It will be appreciated by those of ordinary skills in the art that X-ray powder diffraction patterns have certain measurement errors, and depending on the measurement conditions, the intensities of the various spectral lines in the X-ray powder diffraction patterns fluctuate with the conditions, and the relative intensities also vary with the conditions, so there is no need to consider the precise order of magnitude of intensity. In addition, for regular X-ray powder diffraction patterns, the measurement error for a typical diffraction angle is less than 5%. Therefore, the crystalline forms of the present invention are not limited to the crystalline forms that are exactly identical to those disclosed in the drawings of the present invention, but also include any crystalline form with an X-ray powder diffraction pattern substantially equivalent to those shown in the drawings.

$^1$H-NMR is determined by full digital superconducting nuclear magnetic resonance spectrometer AVANCE III. MS is determined by Fourier transform cyclotron resonance mass spectrometer Bruker APEX IV, and C. H, and N are determined by Vario MICRO CUBE elemental analyzer.

Example 1: (4-diethylamino)butylmalonato-(1R, 2R)-(−)-1,2-cyclohexanediamine platinum(II)

(a) Preparation of diethyl 4-bromobutyl malonate 480.516 g (3 mol) of diethyl malonate, 2290.20 g (10.5 mol) of 1,4-dibromobutane and 720 ml of dimethyl sulfoxide were placed in a 5 L three-necked flask and stirred in an ice bath, 125.004 g (3 mol) of sodium hydroxide was added in batches (about 25 g/time, within 2.5 h) at an internal temperature of 8-12° C. The mixture was reacted at this temperature for 1 h. The reaction mixture was kept at 12° C. or lower, and 600 mL of ice water was added dropwise. The reaction mixture was transferred into a separation funnel (the residue in reactor was washed with a little dichloromethane), and the aqueous phase was separated. The organic phase was washed with water (600 ml×3 times), and dried overnight with anhydrous magnesium sulfate.

The desiccant was filtered out. Components of 50-55 mmHg, ≤115° C. (mainly a mixture of diethyl malonate and 1,4-dibromobutane) were collected by distillation under reduced pressure with a water pump, and then the components of 6-8 mmHg, <128° C. were removed by distillation under reduced pressure with an oil pump. The remaining oil is diethyl 4-bromobutyl malonate, a total of 459.46 g, and yield is 51.9%. $^1$H-NMR (CDCl$_3$) (ppm) 4.201 (m, 4H), 3.404 (t, 2H, J=6.7 Hz), 3.323 (t, 1H, J=7.45 Hz), 1.901 (m, 4H, J=7 Hz), 1.495 (m, 2H), 1.272 (t, 6H. J=7.1 Hz), MS (m/z) 333.01, 317.04, 295.05, 281.4.

(b) Preparation of diethyl (4-diethylamino)butyl malonate 213.02 g (1.525 mol) of anhydrous potassium carbonate and 940 ml of acetonitrile were placed in a 3 L three-necked flask and stirred 450.00 g (1.525 mol) of diethyl 4-bromobutyl malonate, 213.02 g (1.525 mol) of diethylamine and 1 L of acetonitrile were then added. The mixture was reacted in an oil bath at 55-60° C., for 5 h TLC test showed that the reaction was terminated. The reaction solution was transferred into a 2 L eggplant-shaped flask, and the solvent was removed by rotary evaporation under reduced pressure with a water pump, 915 ml of isopropyl ether was added and the reaction mixture was stirred while being cooled with an external ice bath, 915 ml of ice water was added at 10-15° C. The mixture was then transferred into a separation funnel to separate the organic phase, and the aqueous phase was extracted with isopropyl ether (610 ml×3 times). The organic phase was combined and placed in a three-necked flask and stirred while being cooled with an external ice salt bath. The temperature of the reaction solution was kept at 5-10° C., and 3050 ml of 0.5 mol/L HCl was added dropwise. The solution was transferred into a separation funnel to separate the isopropyl ether phase, and the aqueous phase was washed with isopropyl ether (915 ml-4 times).

The aqueous phase was placed in a 10 L three-necked flask, and 1830 ml of ethyl acetate was added. The mixture was stirred while being cooled with an external ice salt bath. The reaction solution was kept at 5-10° C., and 3659 ml of 0.5 mol/L NaOH was added dropwise. The solution was then transferred into a separation funnel to separate the organic phase, and the aqueous phase was further extracted with ethyl acetate (915 ml-3 times). The ethyl acetate phase was combined and dried overnight with anhydrous magnesium sulfate. The desiccant was filtered out, and the solvent was removed by evaporation under reduced pressure with suction (42° C., −0.095 MPa) using a water pump. The target product was obtained as an oil, 309.45 g, yield 70.6%. $^1$H-NMR (CDCl$_3$) (ppm) 4.193 (m, 4H), 3.317 (t, 1H, J=7.55 Hz), 2.526 (q, 4H, J=7.15 Hz), 2.404 (m, 2H), 2.040 (s), 1.912 (m, 2H), 1.477 (m, 2H), 1.326 (m, 2H), 1.265 (t, 6H, J=7.15 Hz), 1.006 (t, 6H, J=7.15 Hz). MS(m/z) 288.22.

(c) Preparation of (4-diethylamino)butyl malonate disodium salt 500.00 g (1.7397 mmol) of diethyl (4-diethylamino)butyl malonate oil was added into a 10 L three-necked reaction flask, and stirred magnetically, 2175.0 mL of 90% ethanol aqueous solution of 2 mol/L sodium hydroxide was then added dropwise at an internal temperature of 25±5° C., during which a white solid was precipitated. After the completion of dropping of the alkali liquid, the reaction mixture was heated under reflux for 2 hours, and the reaction end point was monitored by TLC.

After the reaction end point was reached, 3250 mL of anhydrous ethanol was added under reflux. The reaction mixture was then cooled to the internal temperature of 0-5° C., in an ice water bath, stirred and crystallized for 1 h. Solid was filtered out under reduced pressure and then rinsed with anhydrous ethanol (500 mL×3 times). The solid was then dried in a blast oven at 55±5° C., for about 4 h, and 449.7 g of off-white solid was finally obtained, with a yield of 93.9%. The purity detected by HPLC was 99.1%, $^1$H-NMR (D$_2$O) (ppm) 3.15 (t, 1H), 2.40-2.36 (m, 6H), 1.79 (m, 2H), 1.39 (m, 2H), 1.29 (m, 2H), 1.02 (t, 6H).

(d) Preparation of (0R,2R)-(−)-1,2-cyclohexanediamine diiodoplatinum(II)

498.096 g (1.2 mol) of potassium chloroplatinite and 9 L of purified water were added into a 50 L reaction kettle, and potassium chloroplatinite was dissolved with stirring at 20-25° C. under N$_2$ and in dark, 9 L of aqueous solution containing 1593.60 g (9.6 mol) of potassium iodide was added and the mixture was reacted at 50-55° C., for 20 min 6 L of aqueous solution containing 137.04 g (1.2 mol) of (1R,2R)-(−)-1,2-cyclohexanediamine was added, and the reaction was continued at this temperature for 30 min. The temperature was reduced to 20-25° C. The obtained product was filtered under suction, and rinsed with 1350 ml of purified water in multiple times, then with 1350 ml of anhydrous ethanol in multiple times, and finally with 1350 ml of isopropyl ether in multiple times. The product was dried by blowing air at 40° C. 666.56 g of light yellow solid was obtained, with a yield of 98.6%. $^1$HNMR (DMSO-d$_6$) (ppm) 6.5-5.5 (m, 4H), 2.5-1.0 (m, 10H). MS(m/z) 611.85, 580.92.

(e) Preparation of the aqueous nitrate solution of (1R,2R)-(−)-1,2-cyclohexanediamine platinum(II) dihydrate 10 L of purified water and 180.81 g (1.05 mol) of silver nitrate were placed in a 50 L reaction kettle, and (1R,2R)-(−)-1,2-cyclohexanediamine diiodoplatinum(11) and 5 L of purified water were added. The solution was stirred under N$_2$ protection in dark and reacted at 40-45° C. for 6 h. After being cooled to room temperature, the solution was left to stand for 10 minutes and then was filtered. The residue was rinsed with 2917 ml of purified water in multiple times, and the filtrate was combined to obtain a colorless transparent solution, which was used directly for the next reaction.

(f) Preparation of (4-diethylamino)butylmalonato (1R,2R)-(−)-1,2-cyclohexanediamine platinum(II)

289.01 g (1.05 mol) of (4-diethylamino)butyl malonate disodium salt and the aqueous nitrate solution of (1R,2R)-(−)-1,2-cyclohexanediamine platinum(II) dihydrate (1.05 mol) were placed in a 50 L reaction kettle, and stirred under N$_2$ protection in dark. The solution was reacted at 40-45° C., for 6 h, and then was left to stand overnight at room temperature. The reaction solution was concentrated to about 9279 ml by rotary evaporation under reduced pressure with a water pump at 40-45° C. 292.62 g of silica gel for column chromatography (100-200 mesh) with a thickness of 1.5 cm was filled into a suction filtration funnel with an inner diameter of 235 mm, and soaked with purified water. The mixture was then filtered under suction. The residue was rinsed with 2336 ml of purified water in multiple times and combined to obtain a light blue transparent filtrate.

The filtrate was transferred into a 50 L reaction kettle, stirred and cooled in dark. 2054.27 g (2.573 mol) of 5% NaOH aqueous solution was added dropwise at 4-8° C., for 10 min, and a large amount of white solid was produced. The temperature was kept at 4-8° C., and the mixture was stirred for 30 min. The mixture was filtered under suction, and rinsed with 1.5 L of purified water in multiple times. The product was dried overnight by blowing air at 40° C., and was then ground and sieved with an 80 mesh sieve 443.22 g of white powder was obtained, with a yield of 78.4%. The compound of Example 1 was insoluble in water.

$^1$H-NMR (DMSO-d$_6$) (ppm) 5.911 (m, 2H), 5.225 (m, 2H), 3.492 (t, 1H, J=6.7 Hz), 2.415 (q, 4H), 2.315 (t, 2H), 1.793 (m, 4H), 1.357 (m, 2H), 0.929 (t, 6H, J=7.1 Hz) MS (m/z) 539.21866; and elemental analysis: C55.27%, H5.08%, N3.03%.

X-ray powder diffraction was determined by Bruker GADDS. The powder sample was placed into a 1 mm thin-walled capillary tube. The capillary tube was rotated during data acquisition. The distance between the sample and the detector was 17 cm, the radiation ray was CuKα (45 Kv, 110 mA, λ=1.54060 Å), data was collected from 3°<2θ<50°, and the exposure time of the sample was 70 seconds.

FIG. 1 is an X-ray powder diffraction pattern of 2-(4-diethylamino)butylmalonato-(1R,2R)-(−)-1,2-cyclohexanediamine platinum(II), exhibiting a large number of diffraction peaks.

The representative peaks of XRPD are shown in Table 1.

Table 1

TABLE 1

| Diffraction angle (°2θ) | D value (Å) | Relative intensity (%) |
|---|---|---|
| 4.380 | 20.158 | 99.3 |
| 8.754 | 10.092 | 37.0 |
| 12.241 | 7.725 | 16.7 |
| 13.177 | 6.714 | 13.0 |
| 17.041 | 5.194 | 42.7 |
| 17.594 | 5.037 | 28.7 |
| 18.056 | 4.909 | 6.7 |
| 18.622 | 4.761 | 7.7 |
| 19.186 | 4.622 | 8.8 |
| 19.553 | 4.536 | 6.1 |
| 19.981 | 4.440 | 6.4 |
| 20.409 | 4.348 | 59.6 |
| 21.736 | 4.085 | 32.4 |
| 22.514 | 3.946 | 5.0 |
| 22.854 | 3.727 | 12.0 |
| 24.54 | 3.625 | 7.5 |
| 24.895 | 3.574 | 6.8 |
| 25.320 | 3.515 | 10.5 |
| 26.517 | 3.359 | 12.7 |
| 27.870 | 3.199 | 5.0 |

The crystalline characteristic of the compound in Example 1 can also be characterized by the X-ray powder diffraction pattern (CuKα, λ=1.54060 Å, at about 25° C.) of the following data, including 2θ value selected from the followings: 4.3±0.2, 8.7±0.2, 12.2±0.2, 13.2±0.2, 17.0±0.2, 17.6±0.2, 20.4±0.2, 21.7±0.2, 22.8±0.2, 25.3±0.2, and 26.5±0.2.

Example 2

2-(4-diethylamino)butylmalonato-(1R,2R)-(−)-1,2-cyclohexanediamine platinum(II) tosylate 3.50 g (6.51 mmol) of 2-(4-diethylamino)butylmalonato-(1R,2R)-(−)-1,2-cyclohexanediamine platinum(II) free base was suspended in 100 mL of methanol, and stirred at room temperature. 20 mL of a methanol solution containing 1.311 g (7.62 mmol) of p-toluenesulfonic acid was added dropwise, and then the solution was further stirred and reacted for 1 hour. The solution was colorless and transparent. Activated carbon was added to the solution for decolorization. The solution was then filtered, and part of the solvent methanol was removed under reduced pressure. Ethyl acetate was added for cooling and crystallization, and the solid was filtered and collected with a Buchner funnel, which was dried under reduced pressure and vacuum to obtain 4.62 g of white powdery target product, with a yield of 97.6%.

Figure 2:
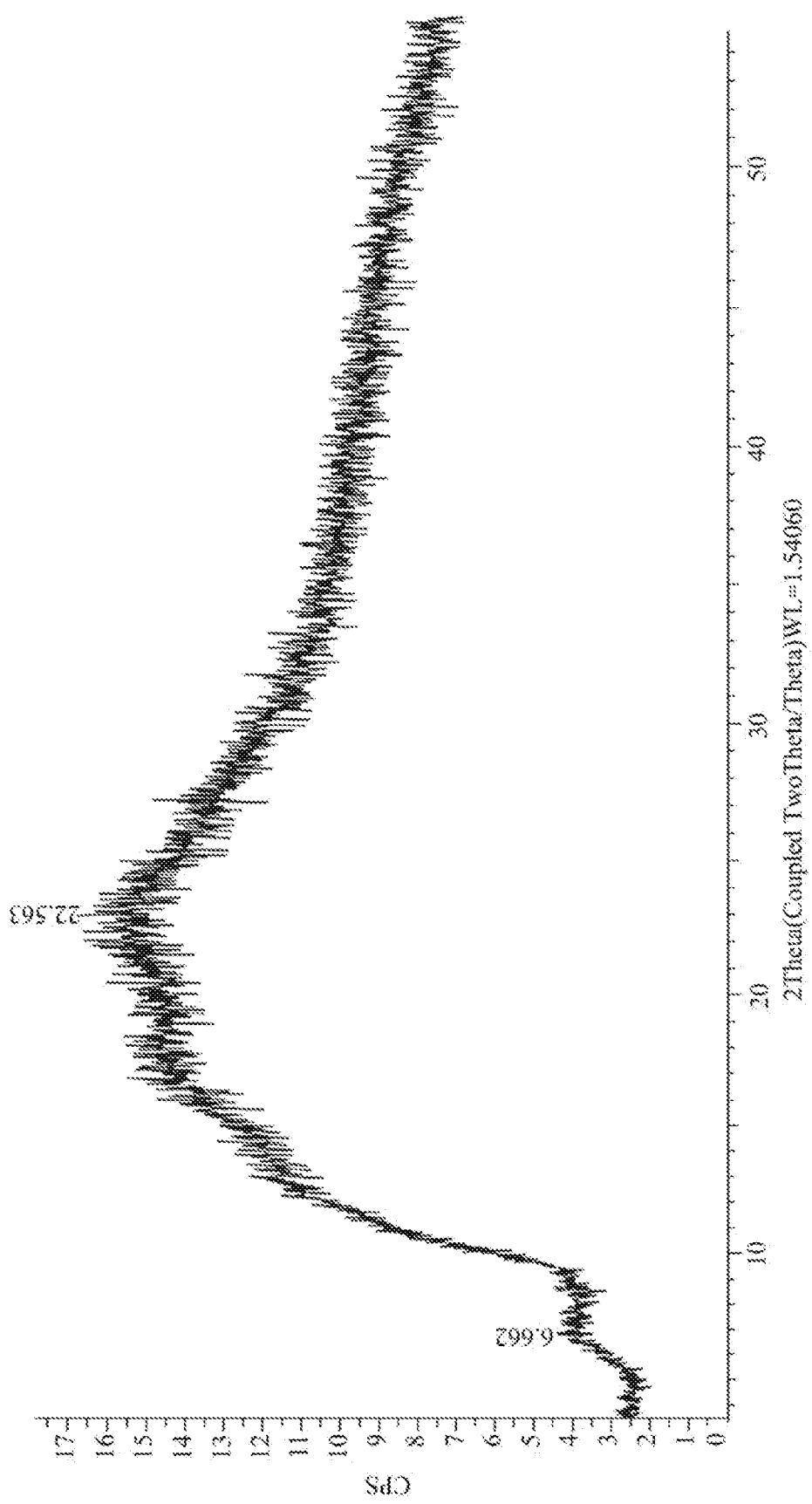
FIG. 2: X-ray powder diffraction pattern of (4-diethylamino)butylmalonato-(1R,2R)-(−)-1,2-cyclohexanediamine platinum(II) tosylate.

FIG. 2 is an X-ray powder diffraction pattern of 2-(4-diethylamino)butylmalonato-(1R,2R)-(−)-1,2-cyclohexanediamine platinum(II) tosylate, which shows that the compound has no diffraction peak.

Example 3

2-(4-diethylamino)butylmalonato-(1R,2R)-(−)-1,2-cyclohexanediamine platinum(II) mesylate 2.50 g (4.64 mmol) of 2-(4-diethylamino)butylmalonato-(1R,2R)-(−)-1,2-cyclohexanediamine platinum(II) free base was suspended in 50 mL of methanol, and stirred at room temperature. 50 mL of a methanol solution containing 0.47 g (4.87 mmol) of methanesulfonic acid was added dropwise, and then the solution was further stirred and reacted for 1 hour. The solution was colorless and transparent. Activated carbon was added to the solution for decolorization. The solution was then filtered, and part of the solvent methanol was removed under reduced pressure. Ethyl acetate was added for cooling and crystallization, and the solid was filtered and collected with a Buchner funnel, which was dried under reduced pressure and vacuum to obtain 2.95 g of white powdery target product, with a yield of 99.5%.

Figure 3:
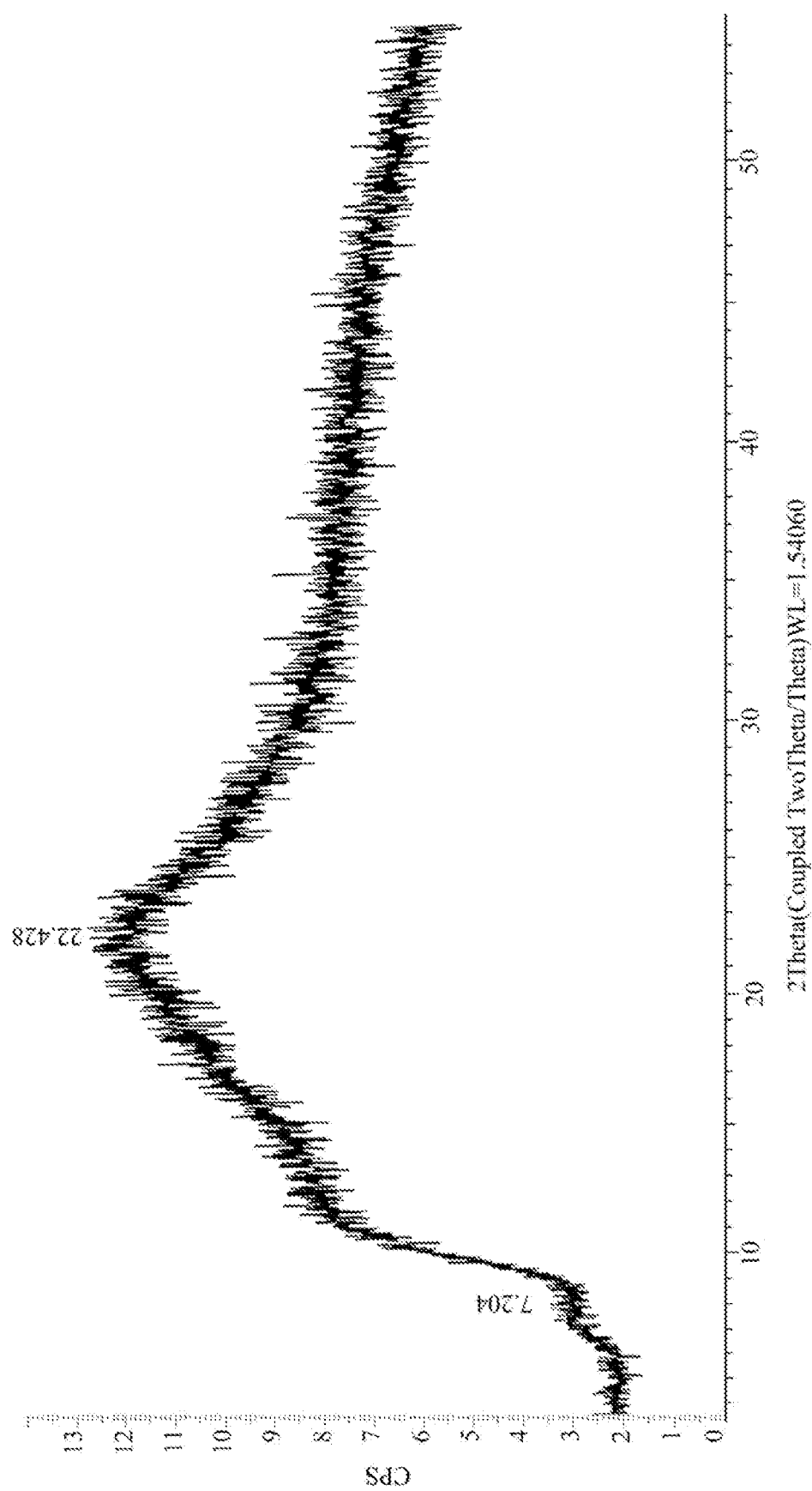
FIG. 3: X-ray powder diffraction pattern of (4-diethylamino)butylmalonato-(1R,2R)-(−)-1,2-cyclohexanediamine platinum(HI) mesylate.

FIG. 3 is an X-ray powder diffraction pattern of 2-(4-diethylamino)butylmalonato-(1R,2R)-(−)-1,2-cyclohexanediamine platinum(II) mesylate, which shows that this compound has no obvious diffraction peak.

Example 4

2-(4-diethylamino)butylmalonato-(1R,2R)-(−)-1,2-cyclohexanediamine platinum(II) L-(+) tartrate 1.20 g (2.23 mmol) of 2-(4-diethylamino)butylmalonato-(1R,2R)-(−)-1,2-cyclohexanediamine platinum(II) free base was suspended in 30 mL of methanol, and stirred at room temperature. 20 mL of a methanol solution containing 0.35 g (2.39 mmol) of L-(+) tartaric acid was added dropwise, and then the solution was further stirred and reacted for 1 hour. The solution was colorless and transparent. Activated carbon was added to the solution for decolorization. The solution was then filtered, and methanol was removed under reduced pressure. Then ethanol was added for dissolving the residue. The solution was cooled and crystallized. The solid was filtered and collected with a Buchner funnel, which was dried under reduced pressure and vacuum to obtain 1.15 g of white powdery target product, with a yield of 74.9%.

Figure 4:
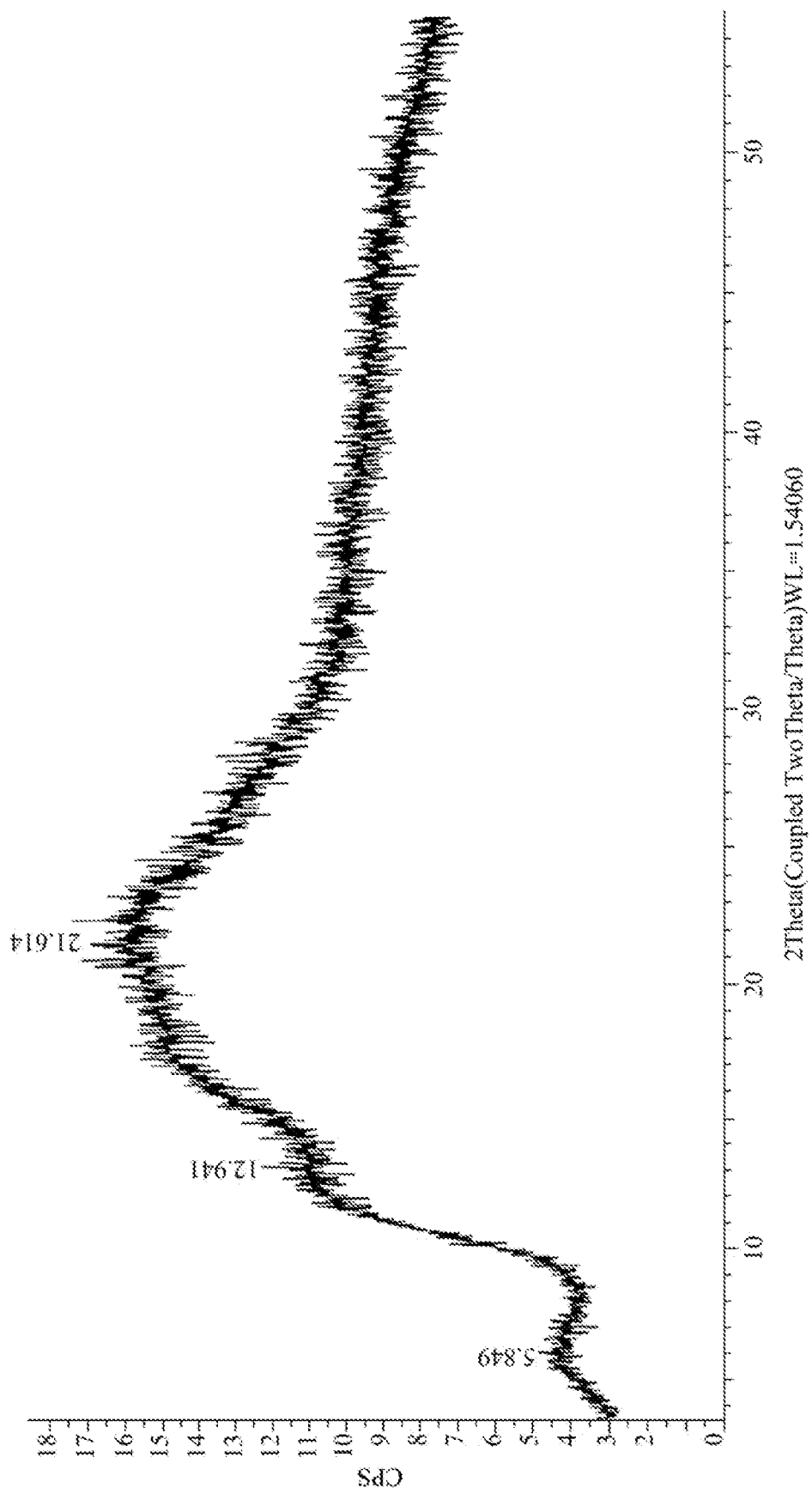
FIG. 4: X-ray powder diffraction pattern of (4-diethylamino)butylmalonato-(1R,2R)-(−)-1,2-cyclohexanedianune platinum(II) L(+) tartrate.

FIG. 4 is an X-ray powder diffraction pattern of 2-(4-diethylamino)butylmalonato-(1R,2R)-(−)-1,2-cy-cyclohexanediamine platinum(II) L-(+) tartrate, which shows that this compound has no obvious diffraction peak.

Example 5 2-(4-diethylamino)butylmalonato-(1R,2R)-(−)-1,2-cyclohexanediamine platinum(II) phosphate 224.04 g (644.937 mmol) of phosphoric acid and 4.5 L of methanol were placed in a 10 L three-necked flask. The mixture was stirred and cooled to −5-0° C., in an ice salt bath. 2-(4-diethylamino)butylmalonato-(1R,2R)-(−)-1,2-cyclohexanediamine platinum(II) was added to the mixture. The residue was washed with 1.3 L of methanol which was precooled to −10 to −5° C. The mixture was reacted at −5-0° C., for 30 min. 292.62 g of silica gel for column chromatography (100-200 mesh) with a thickness of 1.5 cm was filled into a suction filtration funnel with an inner diameter of 235 mm, and soaked with 23.773 L of isopropyl ether. The mixture was then filtered under suction. The residue was rinsed three times with 1.9 L of methanol which was precooled to −5-0° C., and combined to obtain a colorless and transparent filtrate.

The filtrate was placed in a 50 L reaction kettle. 15.39 L of isopropyl ether precooled to 0-5° C. was added to the filtrate with stirring over 5-10 min, and a large amount of white solid was generated. After stirring for 40 mm, the resultant was filtered under suction, and then was repeatedly rinsed with 1.5 L of isopropyl ether precooled to −5-0° C.

6 L of isopropyl ether was placed in a 50 L reaction kettle and cooled to −5-0° C. The filter cake was added to the mixture with stirring. The residue was rinsed multiple times with 2.4 L of isopropyl ether precooled to −5-0° C. The mixture was stirred for 10 mm at −5-0° C., and filtered under suction. The solid was rinsed with isopropyl ether. The solid was dried overnight by blowing air at 40° C. ground and sieved with an 80 mesh sieve, and then dried in vacuum (−0.095 MPa, room temperature, with $P_2O_5$ therein) for 6 h. 360.07 g of 2-(4-diethylamino)butylmalonato-(1R,2R)-(−)-1,2-cyclohexanediamine platinum(II) phosphate white solid was obtained as the product, with a yield of 87.7%.

The crystal prepared by this method is defined as crystal A1.

Figure 5:
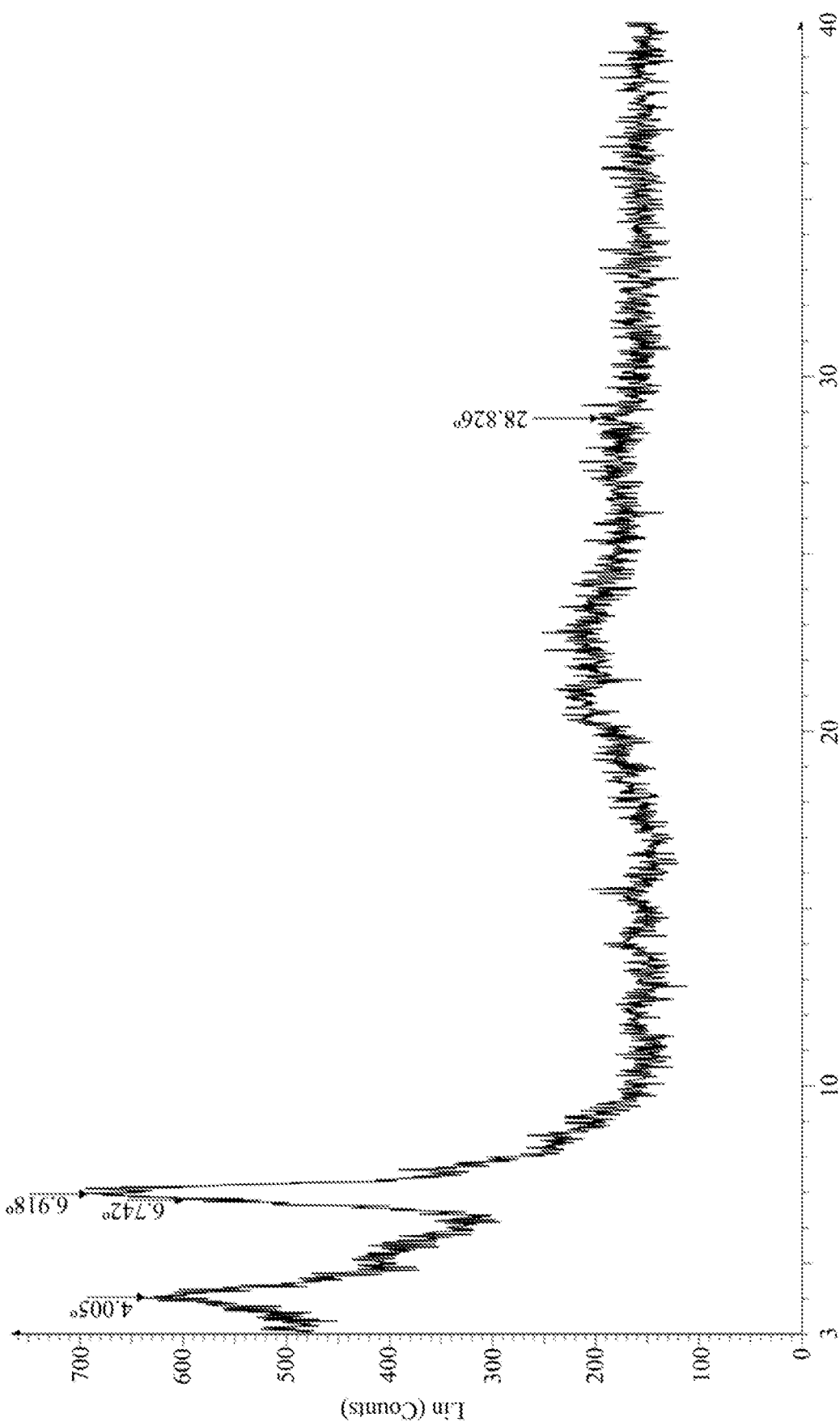
FIG. 5: X-ray powder diffraction pattern of (4-diethylamino)butylmalonato-(1R,2R)-(−)-1,2-cyclohexanediamine platinum(II) phosphate (A1).

FIG. 5 is an X-ray powder diffraction pattern of (4-diethylamino)butylmalonato-(1R,2R)-(−)-1,2-cyclohexanediamine platinum(11) phosphate (Crystal A1). The spectral data is shown in Table 2.

Table 2

| Diffraction angle (2θ) | D value (Å) | Relative intensity (%) |
| --- | --- | --- |
| 4.005 | 22.042 | 91.9 |
| 6.742 | 13.100 | 86.6 |
| 6.918 | 12.767 | 100 |

Crystal (A1) of the compound of Formula (1) is characterized by X-ray powder diffraction pattern (CuKα, λ=1.54060 Å, at about 25° C.), which can also be characterized by the following data, including a 2θ value selected from the followings: 4.0±0.2, 6.7±0.2, and 6.9±0.2.

The above resultant 2-(4-diethylamino)butylmalonato-(1R,2R)-(−)-1,2-cyclohexanediamine platinum(II) phosphate Crystal (A1) was dissolved in 500 mL of sterile water, filtered and lyophilized to obtain 342.7 g of product, with a yield of 95.2%.

The crystalline product prepared by this method was defined as Crystal A2. Three batches of products were subjected to X-ray powder diffraction pattern determination, and the results of the three batches were all consistent with those in FIG. 6, indicating that the preparation of (4-diethylamino)butylmalonato-(1R,2R)-(−)-1,2-cyclohexanediamine platinum(II) phosphate by this method can ensure controllable quality. $^1$H-NMR (DMSO-$d_6$) (ppm) 6.75 (broad peak), 5.90-5.96 (m, 2H), 5.27-5.29 (m, 2H), 3.51-3.55 (t, 1H), 2.82-2.85 (q, 4H), 2.69-2.73 (t, 2H), 2.08 (m, 2H), 1.79-1.83 (m, 2H), 1.79-1.83 (m, 2H), 1.53-1.59 (m, 2H), 1.44-1.15 (m, 2H), 1.22-1.29 (m, 2H), 1.22-1.29 (m, 2H), 1.09-1.13 (t, 6H), 0.97-1.04 (m, 2H).

Figure 6:
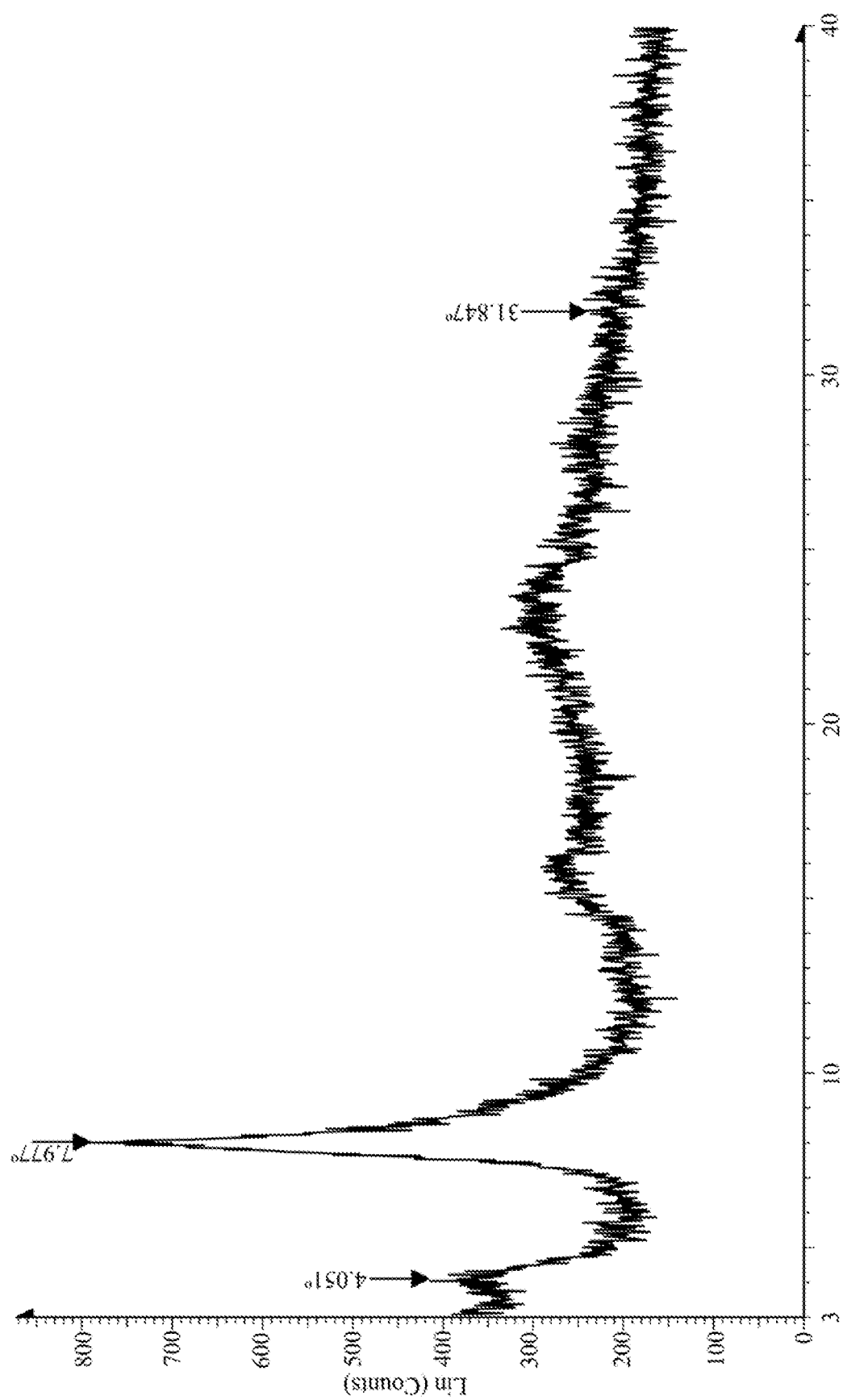
FIG. 6: X-ray powder diffraction pattern of (4-diethylamino)butylmalonato-(1R,2R)-(−)-1,2-cyclohexanediamine platinum(II) phosphate (A2).

FIG. 6 is an X-ray powder diffraction pattern of (4-diethylamino)butylmalonato-(1R,2R)-(−)-1,2-cyclohexanediamine platinum(II) phosphate (Crystal A2). The results are shown in Table 3:

Table 3

TABLE 3

| Diffraction angle (2θ) | D value (Å) | Relative intensity (%) |
| --- | --- | --- |
| 4.051 | 21.794 | 52.5 |
| 7.977 | 11.074 | 100 |
| 31.847 | 2.808 | 30.3 |

Crystal (A2) of the compound of Formula (1) is characterized by X-ray powder diffraction pattern (CuKα, λ=1.54060 Å, at about 25° C.), which can also be characterized by the following data, including a 2θ value selected from the followings: 4.0±0.2, and 8.0±0.2.

Example 6

20 ml of an isopropanol aqueous solution (95:5) was added in a 100 ml three-necked reaction flask. The solution was then cooled to an internal temperature of 0-5° C. by an ice bath. 1.08 g (2.0 mmol) of 2-(4-diethylamino)butylmalonato-(1R,2R)-(−)-1,2-cyclohexanediamine platinum(II) (free base) compound was added to the solution, to make the solid completely suspended in the solution. The mixture was kept at 0-5° C., and stirred for 15 min, and then 5 mL of isopropanol aqueous solution containing 0.235 g (2.40 mmol) of phosphoric acid was added dropwise at an internal temperature of 0-5° C. After the completion of dropping of isopropanol, the solution was kept at an internal temperature of 0-5° C., and crystallized with stirring for 40 min. The solution became completely transparent and the reaction was terminated. Part of isopropanol was removed under reduced pressure, followed by freezing for crystallization. The solid was collected by filtration, and dried under reduced pressure to obtain 1.01 g of 2-(4-diethylamino)butylmalonato-(1R,2R)-(−)-1,2-cyclohexanediamine platinum(II) phosphate, with a yield of 79.4%.

Figure 7:
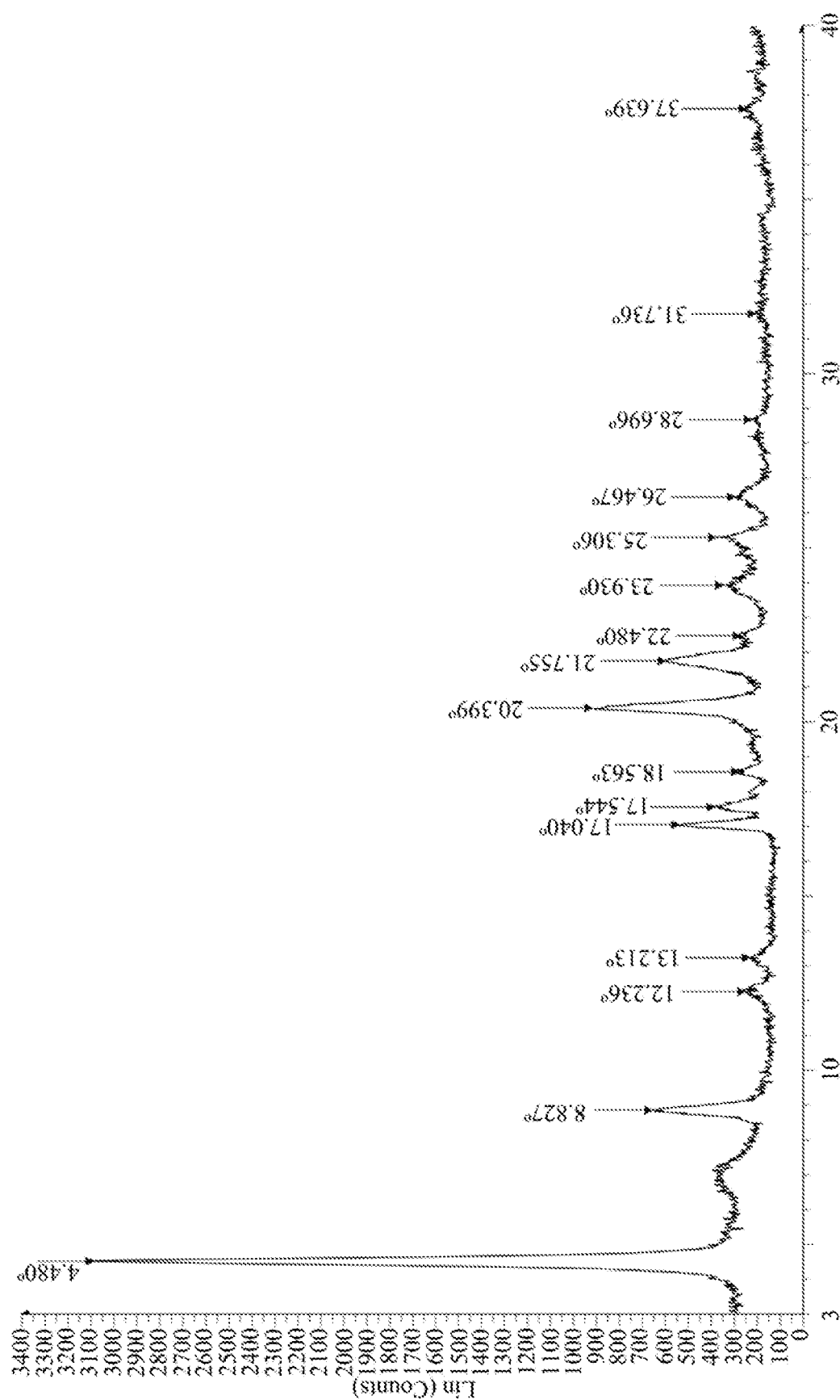
FIG. 7: X-ray powder diffraction pattern of (4-diethylamino)butylmalonato-(1R,2R)-(−)-1,2-cyclohexanediamine platinum(II) phosphate (B).

The crystal prepared by this method is defined as Crystal B. The crystalline form was determined by X-ray powder diffraction. FIG. 7 is an X-ray powder diffraction pattern of 2-(4-diethylamino)butylmalonato-(1R,2R)-(−)-1,2-cyclohexanediamine platinum(II) phosphate (B), which shows that the compound has diffraction peaks.

Table 4

TABLE 4

| Diffraction angle (°2θ) | D value (Å) | Relative intensity (%) |
| --- | --- | --- |
| 4.480 | 19.706 | 100 |
| 8.827 | 10.009 | 21.1 |
| 12.236 | 7.228 | 8.0 |
| 13.213 | 6.695 | 7.0 |
| 17.040 | 5.199 | 17.3 |
| 17.544 | 5.051 | 12.3 |
| 18.563 | 4.776 | 8.9 |
| 20.399 | 4.350 | 29.6 |
| 21.755 | 4.082 | 19.2 |
| 22.480 | 3.952 | 8.7 |
| 23.930 | 3.715 | 11.1 |
| 25.306 | 3.516 | 12.1 |
| 26.467 | 3.365 | 9.4 |

TABLE 4-continued

| Diffraction angle (°2θ) | D value (Å) | Relative intensity (%) |
| --- | --- | --- |
| 28.696 | 3.108 | 7.1 |
| 31.736 | 2.817 | 6.6 |
| 37.639 | 2.388 | 7.8 |

Crystal (B) of the compound of Formula (1) is characterized by X-ray powder diffraction pattern (CuKα, λ=1.54060 Å, at about 25° C.), which can also be characterized by the following data: including a 2θ value selected from the followings: 4.5±0.2, 8.83±0.2, and 20.4±0.2.

Example 7

15 ml of an isopropanol aqueous solution (90:10) was added in a 100 ml three-necked reaction flask. The solution was cooled to an internal temperature of 0-5° C. by an ice bath. 1.08 g (2.0 mmol) of 2-(4-diethylamino)butylmalonato-(1R,2R)-(−)-1,2-cyclohexanediamine platinum(II) (free base) compound was added to the solution, to make the solid completely suspended in the solution. The mixture was kept at 0-5° C., and stirred for 15 min, and then 3 mL of isopropanol: water (90:10) solution containing 0.235 g (2.40 mmol) of phosphoric acid was added dropwise at an internal temperature of 0-5° C. After the completion of dropping of isopropanol, the solution was kept at an internal temperature of 0-5° C., and crystallized with stirring for 30 min. The solution became completely transparent and the reaction was terminated. 10 mL of isopropanol was added dropwise into the solution, followed by freezing for crystallization. The solid was collected by filtration, and dried under reduced pressure to obtain 1.12 g of 2-(4-diethylamino)butylmalonato-(1R,2R)-(−)-1,2-cyclohexanediamine platinum(II) phosphate, with a yield of 88.1%.

The crystal prepared by this method is defined as Crystal C.

Figure 8:
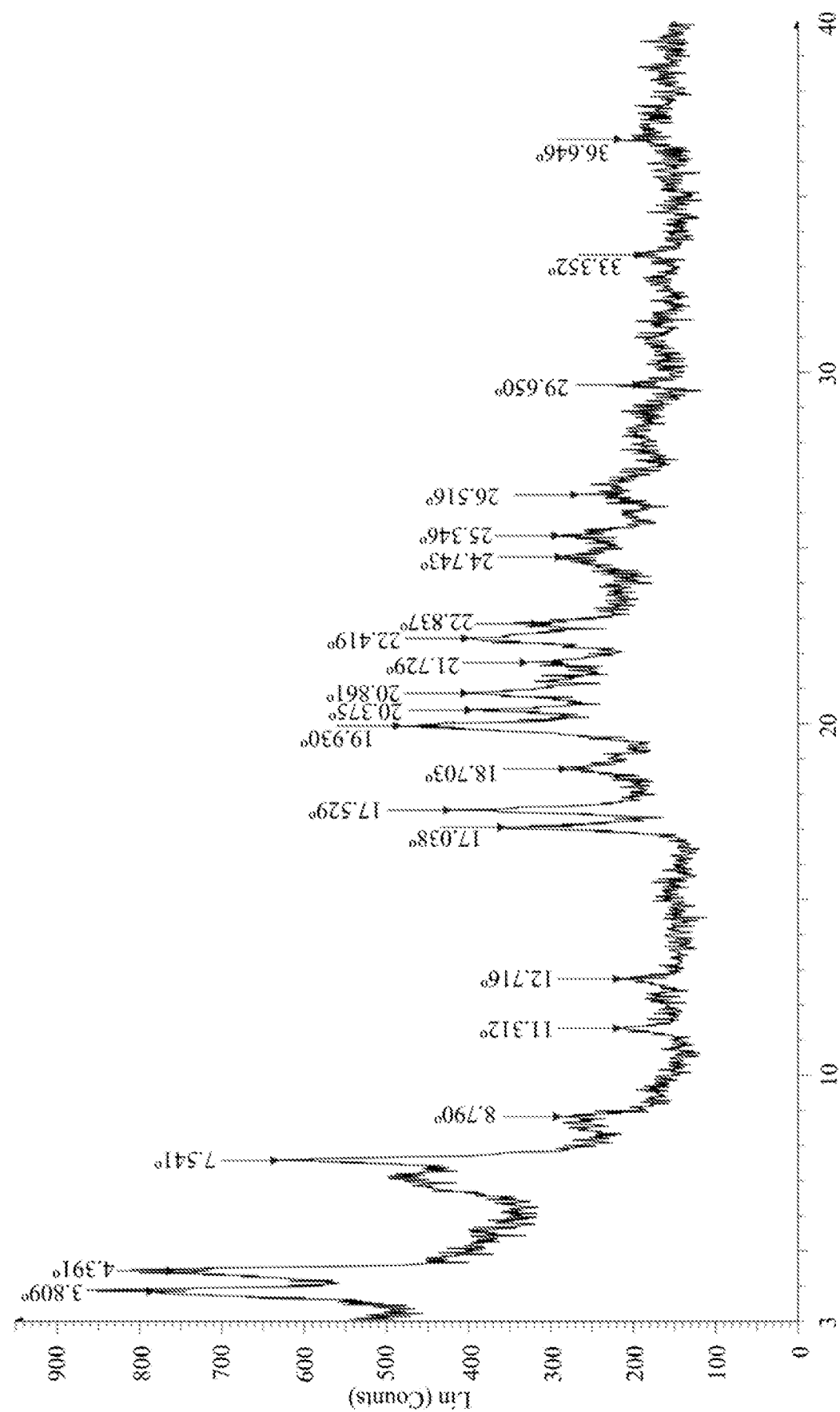
FIG. 8: X-ray powder diffraction pattern of (4-diethylamino)butylmalonato-(1R,2R)-(−)-1,2-cyclohexanediamine platinum(II) phosphate (C).

The crystal form thereof was determined by X-ray powder diffraction. FIG. 8 is an X-ray powder diffraction pattern of 2-(4-diethylamino)butylmalonato-(1R,2R)-(−)-1,2-cyclohexanediamine platinum(II) phosphate (C), which shows that this compound has diffraction peaks.

Table 5

TABLE 5

| Diffraction angle (°2θ) | D value (Å) | Relative intensity (%) |
| --- | --- | --- |
| 3.809 | 23.179 | 100 |
| 4.391 | 20.108 | 96.9 |
| 7.541 | 11.714 | 80.7 |
| 8.790 | 10.051 | 36.7 |
| 11.312 | 7.816 | 27.3 |
| 12.716 | 6.956 | 27.3 |
| 17.038 | 5.200 | 45.3 |
| 17.529 | 5.055 | 53.8 |
| 18.703 | 4.741 | 35.8 |
| 19.930 | 4.451 | 61.7 |
| 20.375 | 4.355 | 50.4 |
| 20.861 | 4.255 | 51.1 |
| 21.729 | 4.087 | 41.9 |
| 22.419 | 3.962 | 51.0 |
| 22.837 | 3.891 | 40.1 |
| 24.743 | 3.595 | 36.4 |
| 25.346 | 3.511 | 36.9 |
| 26.516 | 3.359 | 34.0 |
| 29.650 | 3.011 | 24.3 |
| 33.352 | 2.684 | 24.0 |
| 36.646 | 2.450 | 27.2 |

Crystal (C) of the compound of Formula (1) is characterized by X-ray powder diffraction pattern (CuKα, λ=1.54060 Å, at about 25° C.), which can also be characterized by the following data, including a 2θ value selected from the followings: 3.8±0.2, 4.4±0.2, 7.5±0.2, 19.9±0.2, 20.4±0.2, and 20.8±0.2.

Example 8

22 ml of absolute methanol was added in a 100 nil three-necked reaction flask, and cooled to an internal temperature of −10 to −5° C. in an ice salt bath. Then, 1.08 g (2.0) mmol) of 2-(4-diethylamino)butylmalonato-(1R,2R)-(−)-1,2-cyclohexanediamine platinum(II) (free base) was added, to make the solid completely dissolved in absolute methanol. The mixture was kept at −10 to −5° C. and stirred for 30 min, and then 15 ml of isopropanol solution containing 0.235 g (2.40 mmol) of phosphoric acid was added dropwise at an internal temperature of −5-0° C. After the completion of dropping isopropanol, the mixture was keep at an internal temperature of −5-0° C., and crystallized with stirring for 10 min, and then filtered under reduced pressure to obtain 0.89 g of 2-(4-diethylamino)butylmalonato-(1R, 2R)-(−)-1,2-cyclohexanediamine platinum(I) phosphate, with a yield of 69.9%.

Figure 9:
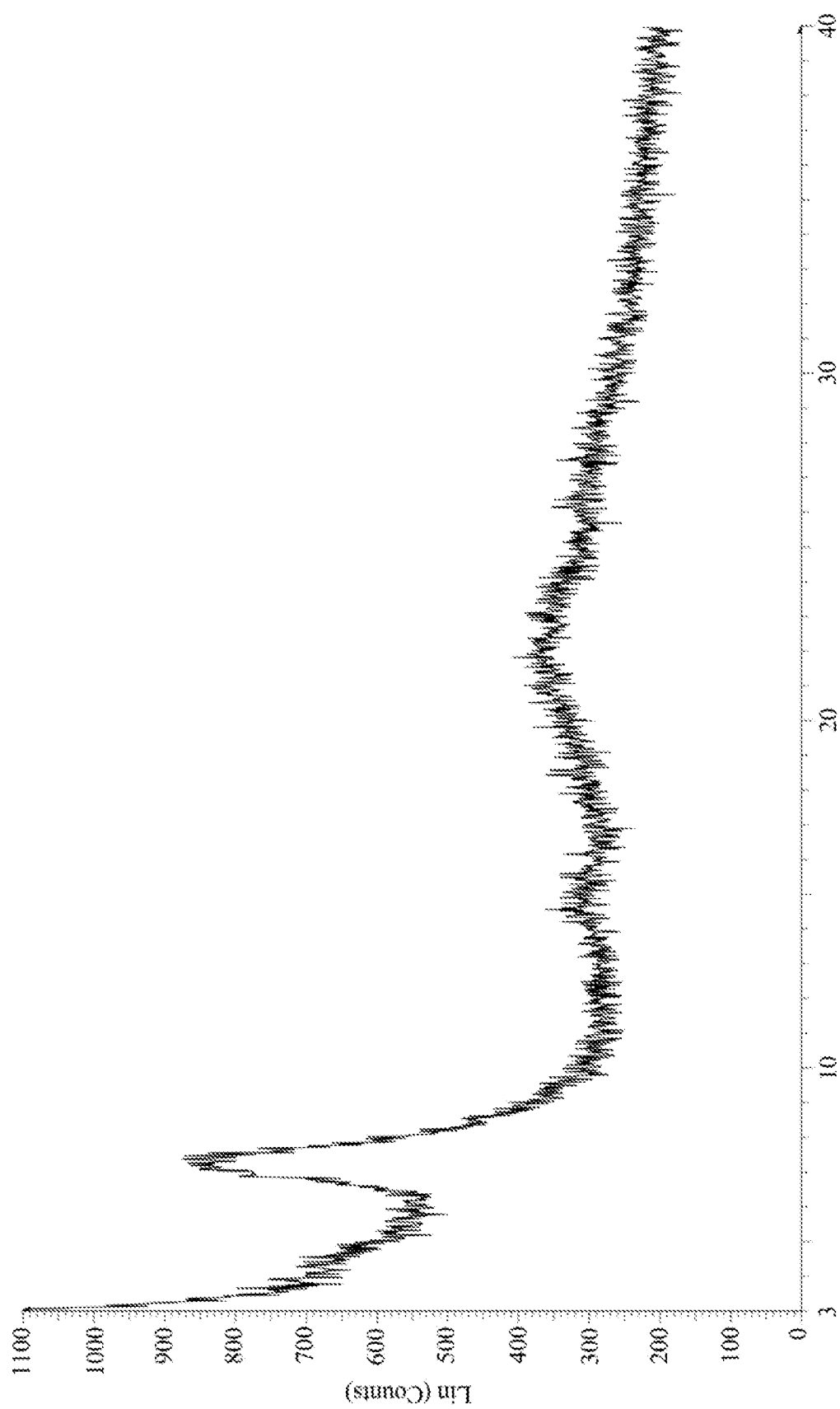
FIG. 9: X-ray powder diffraction pattern of (4-diethylamino)butylmalonato-(1R,2R)-(−)-1,2-cyclohexanediamine platinum(II) phosphate (D).

FIG. 9 is an X-ray powder diffraction pattern of 2-(4-diethylamino)butylmalonato-(1R,2R)-(−)-1,2-cyclohexanediamine platinum(II) phosphate, which shows that the compound has diffraction peaks. The crystal prepared by this method is defined as Crystal D.

Table 6

TABLE 6

| Diffraction angle (2θ) | D value (Å) | Relative intensity (%) |
|---|---|---|
| 3.915 | 21.042 | 90.1 |
| 6.772 | 12.950 | 84.8 |
| 7.108 | 12.668 | 100 |

Crystal (D) of the compound of Formula (1) is characterized by X-ray powder diffraction pattern (CuKα, λ=1.54060 Å, at about 25° C.), which can also be characterized by the following data, including a 2θ value selected from the followings: 3.9±0.2, 6.8±0.2, and 7.1±0.2.

Preparation Example 1

(A2) crystal of the compound of Formula (1) 20 g

Mannitol 50 g

Water for injection adding up to 1000 ml

To produce into 1000 pieces

Process: 20 g of the compound of Formula (1) with low crystallinity and 50 g of mannitol were added into a 1000 ml glassware 1000 ml of water for injection was added at a low temperature (2-8° C.) to dissolve them, and 2.0 g of activated carbon for medicinal use was added. The solution was stirred for 10 min, and then stood for adsorption for 20 min, followed by filtering with a 0.22 μm microfiltration membrane, and then was placed into 2 ml vials. Each vial was filled with 1 ml of the solution, which was then lyophilized to obtain the product at the specification of 20 mg/vial. The product was a white loose block, with a pH value of 4.10.

Preparation Example 2

(A2) crystal of the compound of Formula (1) 100 g

Water for injection adding up to 1000 ml

Process: 50 g of the compound of Formula (1) with low crystallinity was added into a 1000 ml glassware. 100) ml of water for injection was added at a low temperature (2-8° C.) to dissolve the compound, and 2.0 g of activated carbon for medicinal use was added. The solution was stirred for 10 min, and then stood for adsorption for 20 min, followed by filtering with a 0.22 μm microfiltration membrane, and then was placed into 2 ml vials. Each vial was filled with 1 ml of the solution, which was then lyophilized to obtain the product at the specification of 100 mg/vial.

The product was a white loose block, with a pH value of 4.20.

Figure 10:
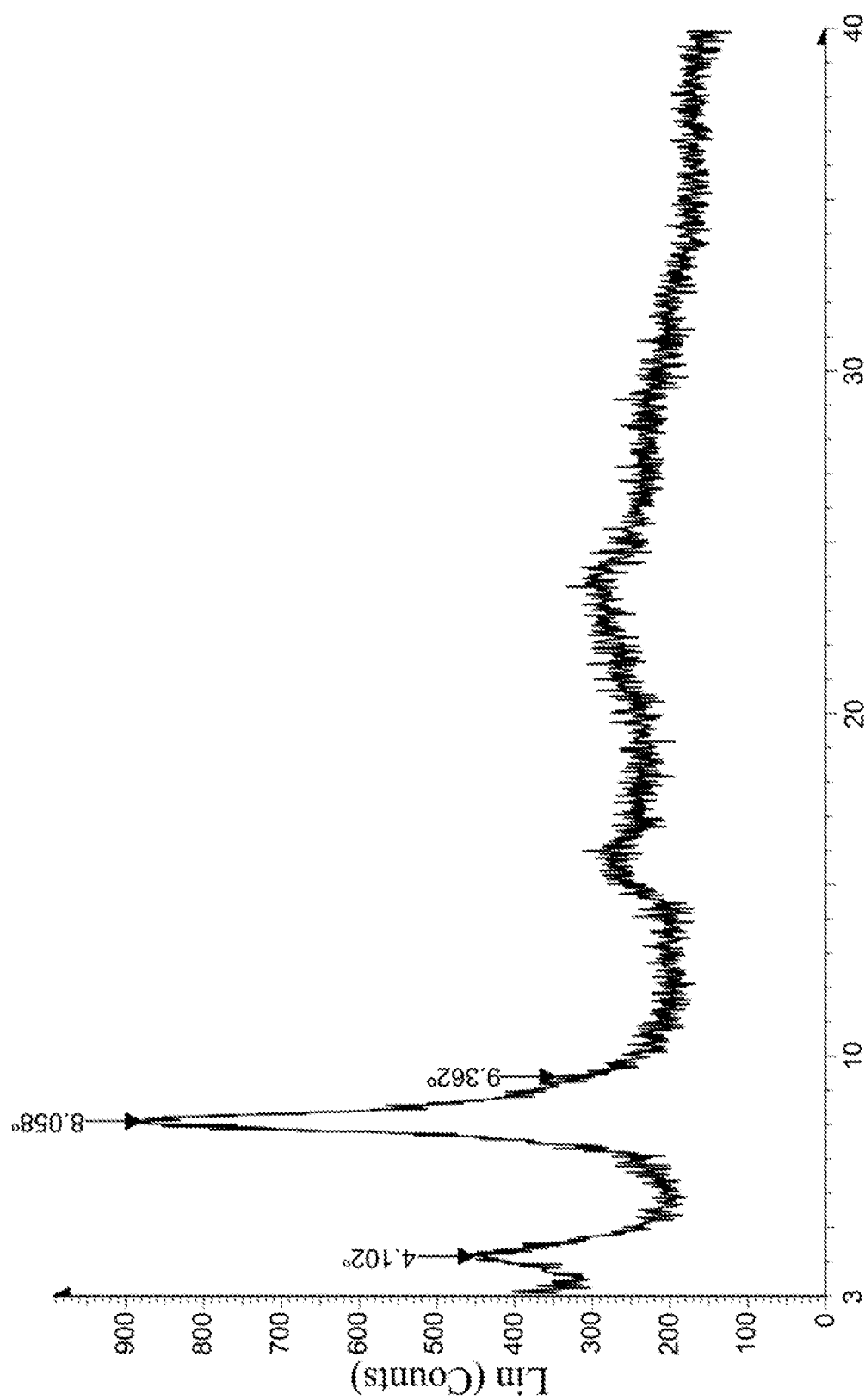
FIG. 10: X-ray powder diffraction pattern of (4-diethylamino)butylmalonato-(1R,2R)-(−)-1,2-cyclohexanediamine platinum(II) phosphate for injection.

The X-ray powder diffraction pattern is shown in FIG. 10, and the diffraction pattern of its crystal form is the same as that of the raw material, exhibiting blunt and wide peak shapes, indicating that there are defects in the crystal, or that the peak shape is affected by the particle size or crystal habit or the like. The 2θ angles of the main diffraction peaks are consistent with those of the raw materials, which indicates that multiple lyophilization with water being used as the solvent will not affect the crystal form. In animal models, pharmacodynamics and toxicology of the drug prove that this crystal form is safe and effective in practice Table 7

TABLE 7

| Diffraction angle (2θ) | D value (Å) | Relative intensity (%) |
|---|---|---|
| 4.102 | 21.524 | 51.2 |
| 8.058 | 10.963 | 100.0 |
| 9.362 | 9.439 | 39.2 |

The crystal of the lyophilized preparation of the compound of Formula (1) is characterized by X-ray powder diffraction pattern (CuKα, λ=1.54060 Å, at about 25° C.), which can also be characterized by the following data, including a 2θ value selected from the followings: 4.1±0.2, and 8.0±0.2.

Preparation Example 3

(A2) crystal of the compound of Formula (1) 20 g

Sodium dihydrogen phosphate-disodium hydrogen phosphate buffer adding up to 100 ml Process: 20) g of the compound of Formula (1) with low crystallinity was added into a 200) ml glassware. 100 ml of sodium dihydrogen phosphate-disodium hydrogen phosphate buffer (pH of 6.0) was added at a low temperature (2-8° C.) to dissolve the compound, and 0.5 g of activated carbon for medicinal use was added. The solution was stirred for 10 min, and then stood for adsorption for 20 min, followed by filtering with a 0.22 μm microfiltration membrane, and then was placed into 2 ml vials. Each vial was filled with 1 ml of the solution, which was then lyophilized to obtain the product at the specification of 200 mg/vial.

The product is a white loose block, with a pH value of 4.67.

Experimental examples: solubility and hygroscopicity experiments of various salts of 2-(4-diethylamino)butylmalonato-(1R,2R)-(−)-1,2-cyclohexanediamine platinum(II)

| | | | Hygroscopicity experiments | | | | | | |
|---|---|---|---|---|---|---|---|---|---|
| | | 25° C. ± 1° C.; relative humidity 44% ± 2% | | | | 25° C. ± 1° C.; relative humidity 69% ± 2% | | | |
| | | 1 h | | 24 h | | 1 h | | 24 h | |
| Salt name | Status | Status | Hygroscopicity (%) | Status | Hygroscopicity (%) | Status | Hygroscopicitye (%) | Status | Hygroscopicity (%) | Solubility (mg/mL) |
| Phosphate salt (A1) | White powder | White powder | 2.09 | White powder | 5.89 | White powder | 2.79 | White powder | 8.86 | Greater than 500 |
| Phosphate salt (A2) | White powder | White powder | 1.79 | White powder | 3.98 | White powder | 2.02 | White powder | 4.32 | Greater than 500 |
| Phosphate (B) | White powder | White powder | 1.98 | White powder | 4.79 | White powder | 2.93 | White powder | 8.58 | Greater than 500 |
| Phosphate salt (C) | White powder | White powder | 2.21 | White powder | 6.32 | White powder | 3.45 | White powder | 9.36 | Greater than 500 |
| Phosphate salt (D) | White powder | White powder | 2.32 | White powder | 7.63 | White powder | 3.43 | White powder | 10.76 | Greater than 500 |
| Tosylate salt | White powder | Viscous solid | 4.56 | Light gray-white viscous substance | 8.78 | Viscous solid | 5.30 | Light gray-white viscous substance | 9.86 | Greater than 500 |
| Mesylate salt | White powder | Viscous solid | 4.98 | Light gray viscous blocky solid | 9.89 | Viscous solid | 6.37 | Light gray blocky viscous solid | 13.89 | Greater than 500 |
| L(+) tartrate salt | White powder | Viscous solid | 4.88 | Light gray viscous blocky solid | 9.76 | Viscous solid | 5.78 | Light gray-white blocky viscous solid | 12.79 | Greater than 500 |
| Fumarate salt | White powder | Viscous solid | 5.87 | Semi-transparent viscous substance | 10.83 | Viscous solid | 6.83 | Semi-transparent viscous substance | 13.90 | Greater than 500 |
| Butyrate salt | White powder | Viscous solid | 5.36 | Light gray viscous blocky solid | 11.21 | Viscous solid | 5.69 | Light gray-white blocky viscous solid | 12.76 | 358 |

What I claim is:

1. A platinum compound shown in the structure of Formula (1):

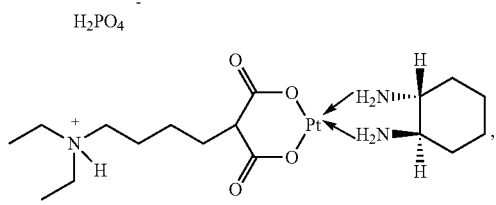

having characteristic peaks at 2θ values of 4.0±0.2 an 8.0±0.2 in X-ray powder diffraction, wherein the peak at 8.0±0.2 has a relative intensity of 100% and the peak at 4.0±0.2 has a relative intensity of 52.5±0.5%.

2. The platinum compound according to claim 1, having characteristic peaks of X-ray powder diffraction pattern shown in FIG. 6.

3. A pharmaceutical composition comprising the compound of claim 2.

4. A pharmaceutical composition comprising the compound of claim 1.

5. A method for preparing the platinum compound according to claim 1, comprising the steps of:
(1) preparing a 4-diethylamino butylmalonate disalt solution, and adding a solvent to crystallize and obtain 4-diethylamino butylmalonate disalt, wherein the solvent is selected from methanol, ethanol, isopropanol, acetonitrile, acetone, dimethyl sulfoxide (DMSO), or mixtures thereof,
(2) preparing (1R,2R)-(−)-1,2-cyclohexanediamine platinum(II) dihydrate salt by: preparing (1R,2R)-(−)-1,2-cyclohexanediamine diiodoplatinum(II), and reacting (1R,2R)-(−)-1,2-cyclohexanediamine diiodoplatinum (II) with silver nitrate in a solvent, wherein the molar ratio of (1R,2R)-(−)-1,2-cyclohexanediamine diiodoplatinum(II) to silver nitrate is 1-3:1; the solvent is selected from water, methanol, ethanol, isopropanol, etc.; the reaction temperature ranges from 0° C., to 60° C.; and the reaction time is 2-10 hours;
(3) preparing the compound of Formula (1) using (4-diethylamino)butylmalonate disalt and (1R,2R)-(−)-1,2-cyclohexanediamine platinum(II) dihydrate salt; and
(4) dissolving the compound of Formula (1) in water, followed by lyophilization to obtain a final crystalline product.

6. The preparation method according to claim 5, wherein the solvent in step (1) is ethanol.

7. The preparation method according to claim 5, wherein the molar ratio of (1R,2R)-(−)-1,2-cyclohexanediamine diiodoplatinum(II) to silver nitrate in step (2) is 1:1.

8. The preparation method according to claim 5, wherein the solvent in step (2) is water.

9. The preparation method according to claim 5, wherein the reaction temperature in step (2) is 40° C.-50° C.

10. The preparation method according to claim 5, wherein the reaction time in step (2) is 5-6 hours.

11. The preparation method according to claim 5, wherein the reaction time for step (2) is 5-6 hours.

* * * * *